United States Patent [19]

Oliphant

[11] Patent Number: 5,501,734
[45] Date of Patent: Mar. 26, 1996

[54] YARN COATING ASSEMBLY AND APPLICATOR

[75] Inventor: Larry J. Oliphant, Swisher, Iowa

[73] Assignee: Gillette Canada, Inc., Kirkland, Canada

[21] Appl. No.: 249,516

[22] Filed: May 26, 1994

Related U.S. Application Data

[63] Continuation-in-part of Ser. No. 151,707, Nov. 12, 1993, abandoned, which is a continuation-in-part of Ser. No. 832,151, Feb. 6, 1992, Pat. No. 5,353,820.

[51] Int. Cl.$^6$ ...................................................... B05C 3/12
[52] U.S. Cl. .............................. 118/234; 68/200; 118/216; 118/255; 118/405; 118/420; 118/428; 118/683; 118/694; 118/712
[58] Field of Search ..................................... 118/123, 216, 118/234, 255, 401, 405, 420, 428, 429, 674, 683, 686, 694, 712, DIG. 18, DIG. 19, DIG. 22; 68/200, 205 R; 239/548, 566; 65/529

[56] References Cited

U.S. PATENT DOCUMENTS

| | | | |
|---|---|---|---|
| 174,619 | 3/1876 | Clark, Jr. ................................ | 132/321 |
| 290,678 | 12/1883 | Gourdiat ................................ | 68/202 |
| 660,943 | 10/1900 | Bavermeister ......................... | 427/2.31 |
| 2,325,129 | 7/1943 | Hardy ................................ | 118/DIG. 22 |
| 2,667,443 | 1/1954 | Ashton ................................ | 433/216 |
| 2,700,636 | 1/1955 | Ashton ................................ | 424/443 |
| 2,748,781 | 6/1956 | Collat ................................ | 132/325 |
| 3,412,192 | 11/1968 | Clapson ................................ | 264/280 |
| 3,492,131 | 1/1970 | Schlatter ................................ | 426/548 |
| 3,507,250 | 4/1970 | Dew, Jr. ................................ | 118/234 |
| 3,615,671 | 10/1971 | Shoaf et al. .......................... | 426/96 |
| 3,642,491 | 2/1972 | Schlatter ................................ | 426/548 |
| 3,699,979 | 10/1972 | Muhler et al. ........................ | 132/321 |
| 3,771,536 | 11/1973 | Dragan ................................ | 132/321 |
| 3,800,046 | 3/1974 | Schlatter ................................ | 426/548 |
| 3,828,419 | 8/1974 | Wanner ................................ | 228/36 |
| 3,830,246 | 8/1974 | Gillings ................................ | 132/321 |
| 3,837,351 | 9/1974 | Thornton ................................ | 132/321 |
| 3,838,702 | 10/1974 | Standish et al. ...................... | 132/321 |
| 3,896,824 | 7/1975 | Thornton ................................ | 132/321 |
| 3,897,795 | 8/1975 | Engel ................................ | 132/321 |
| 3,906,757 | 9/1975 | Arimoto et al. ...................... | 68/20 |
| 3,923,003 | 12/1975 | Carden ................................ | 118/405 |
| 3,943,949 | 3/1976 | Ashton et al. ........................ | 132/321 |
| 3,972,214 | 8/1976 | Jagersberger ......................... | 72/132 |
| 3,991,704 | 11/1976 | Hulstein et al. ...................... | 118/684 |
| 4,000,964 | 1/1977 | Newton ................................ | 8/487 |
| 4,008,727 | 2/1977 | Thornton ................................ | 132/321 |
| 4,013,435 | 3/1977 | Kane et al. ........................... | 65/500 |
| 4,029,113 | 6/1977 | Guyton ................................ | 132/321 |
| 4,033,365 | 7/1977 | Klepak et al. ........................ | 132/321 |
| 4,047,271 | 9/1977 | Peterson et al. ...................... | 28/220 |
| 4,068,615 | 1/1978 | LeNir ................................ | 118/405 |

(List continued on next page.)

FOREIGN PATENT DOCUMENTS

| | | |
|---|---|---|
| 0080440 | 6/1983 | European Pat. Off. |
| 0335466 | 10/1989 | European Pat. Off. |
| 560937 | 10/1932 | Germany ................................ 68/200 |
| 2216803 | 10/1989 | United Kingdom . |

Primary Examiner—David L. Lacey
Assistant Examiner—Laura E. Edwards
Attorney, Agent, or Firm—Oblon, Spivak, McClelland, Maier & Neustadt

[57] ABSTRACT

An apparatus and method for applying coatings to yarns, particularly yarns to be utilized as dental floss. In a preferred arrangement, an array of parallel spaced yarns are continuously fed while being intermittently deflected by a cam or deflector. As the yarns are deflected, they enter a grooved liquid applicator, with the grooves maintaining a predetermined amount of liquid therein by capillary action. A predetermined amount of liquid is thus applied at intermittent or spaced locations along the length of the yarn. The method and apparatus is particularly suitable for providing dye at spaced locations along a continuous length of floss, thereby demarcating lengths suitable for individual use. Various aspects are also applicable to a variety of yarn coating and/or dyeing applications.

15 Claims, 8 Drawing Sheets

U.S. PATENT DOCUMENTS

| | | | |
|---|---|---|---|
| 4,071,615 | 1/1978 | Barth | 424/52 |
| 4,073,260 | 2/1978 | Bosworth et al. | 118/670 |
| 4,096,611 | 6/1978 | Heyner | 28/220 |
| 4,142,538 | 3/1979 | Thornton | 132/321 |
| 4,153,961 | 5/1979 | Cleveland | 8/149 |
| 4,158,976 | 6/1979 | Ditges | 83/157 |
| 4,291,017 | 9/1981 | Beierle et al. | 424/52 |
| 4,350,311 | 9/1982 | Pokhodnya et al. | 242/362.1 |
| 4,414,990 | 11/1983 | Yost | 132/321 |
| 4,548,219 | 11/1985 | Newman et al. | 132/321 |
| 4,605,573 | 8/1986 | Deeg et al. | 427/424 |
| 4,627,975 | 12/1986 | Lynch | 424/49 |
| 4,638,823 | 1/1987 | Newman et al. | 132/321 |
| 4,737,904 | 4/1988 | Ominato | 364/167.01 |
| 4,738,866 | 4/1988 | Conklin et al. | 118/712 |
| 4,789,858 | 2/1988 | Pesce | 132/321 |
| 4,817,643 | 4/1989 | Olson | 132/329 |
| 4,891,960 | 1/1990 | Shah | 118/420 |
| 4,908,153 | 3/1990 | Kossmann et al. | 204/300 EC |
| 4,911,927 | 3/1990 | Hill et al. | 424/443 |
| 4,926,661 | 5/1990 | Agers et al. | 68/200 |
| 4,932,092 | 6/1990 | Yoshida | 8/149 |
| 4,952,392 | 8/1990 | Thame | 424/58 |
| 4,974,615 | 12/1990 | Doundoulakis | 132/321 |
| 4,986,288 | 1/1991 | Kent et al. | 132/321 |
| 4,996,056 | 2/1991 | Blass | 424/443 |
| 4,998,978 | 3/1991 | Varum | 132/321 |
| 5,033,488 | 7/1991 | Curtis et al. | 132/321 |
| 5,042,343 | 8/1991 | Boyadjian | 83/208 |
| 5,063,948 | 11/1991 | Lloyd | 132/321 |
| 5,072,691 | 12/1991 | Strandberg, Jr. et al. | 118/712 |
| 5,181,401 | 1/1993 | Hodan | 68/200 |

YARN COATING ASSEMBLY AND APPLICATOR

This application is continuation-in-part of application Ser. No. 08/151,707, filed Nov. 12, 1993, now abandoned, which is a continuation-in-part of application Ser. No. 07/832,151, filed Feb. 6, 1992, now U.S. Pat. No. 5,353,820.

FIELD OF THE INVENTION

The invention relates to an assembly for dyeing and/or coating selected portions of a yarn during the manufacture of dental floss yarn. In particular it relates to an assembly and a method for dyeing and/or polymer coating selected portions of a yarn as the yarn is traveling at a high speed. The arrangement is particularly suitable for providing a dye and/or polymer coating to selected portions of a dental floss yarn.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes and any similar article.

To improve the effectiveness and convenience of dental flosses, dental flosses combining a thin "floss" portion and a thickened "brush" portion, together with a threader have been developed. The brush portion, when drawn between tooth surfaces, has been found to provide an improved cleaning action which removes materials left by the floss portion, when used alone. The combination provides a substantially superior cleaning action. Such a device is described in U.S. Pat. No. 4,008,727, for example. The complexity of this product requires that each floss segment be individually manufactured and that the product be packaged as bundles of the individual, separate floss articles.

A continuous yarn having brush segments separated by thinner segments is disclosed in U.S. Pat. Nos. 4,008,727 and 4,142,538.

A problem arising in the manufacturing process of continuous floss brushes involves the application of coatings to the yarn. A variety of assemblies and methods are known for providing a yarn with a coating at spaced locations. For example, in one arrangement, a roller receives a coating from a supply, and provides a coating to the yarn as the yarn passes there over in contact with the roller. The roller can be formed with only a partial section of a cylinder, such that only intermittent portions of the yarn contact the roller as the roller rotates. However, such an arrangement has been unsatisfactory in providing an adequate coating to the yarn, particularly in high speed manufacturing assemblies, for example, in which the yarn is traveling at over 100 meters/min., possibly even as high as 160 meters/min.

OBJECTS AND SUMMARY OF THE INVENTION

It is an object of the present invention to provide a yarn coating assembly and method which applies a coating material to a yarn travelling at high speed, at precise and predetermined intervals along the yarn.

It is a further object of the present invention to provide a yarn coating method and assembly which can provide an appropriate amount of a coating material to a yarn while minimizing wastage of the coating material.

It is another object of the invention to provide a method and an assembly for coating selected portions of a yarn under tension such that the selected portions are maintained at a reduced diameter by the coating material after the tension is released.

It is yet another object of the present invention to provide a yarn coating assembly which can coat a plurality of yarns simultaneously, with a continuous supply of coating material provided for intermittent coating of the plurality of yarns.

It is yet another object of the invention to provide a coating applicator for applying a coating material to a yarn, comprising a container for supporting a coating material wherein the level of the coating material in the container is determined by capillary action.

According to the invention there is provided a coating applicator for applying a coating to a yarn, comprising a container wherein the container has at least one open-ended slot, each slot having a base and an open end for receiving a section of yarn, and being dimensioned to support a predetermined amount of a coating material, wherein the container has an upstream and a downstream face, at least the upstream face of the container being inclined inwardly towards the open end, and wherein the open-ended slot is defined by a pair of opposed surfaces extending between the base and the open end, the surfaces being inclined outwardly towards the open end.

The slot may be dimensioned to support the predetermined amount of coating material by capillary action.

The slot may narrow from the upstream face to the downstream face.

Further according to the invention there is provided a yarn coating assembly for applying a coating material to a length of yarn comprising a container means for holding a quantity of the coating material, a drive means for moving the length of yarn past the container means, and displacement means for displacing at least a portion of the yarn toward the container means to bring a section of the yarn into contact with the coating material. The displacement means may comprise a cam on a rotatable wheel, the cam having a cam surface positioned relative to the yarn such that, upon rotation of the wheel, the yarn is urged into contact with the coating material by the cam surface engaging the yarn, and when the cam surface is not in contact with the yarn, the yarn is not in contact with the coating material. The cam may be removably mounted on the wheel to permit replacement with differently sized or differently shaped cams.

The container means may define an open-ended slot having a width sufficient to accommodate the thickness of the yarn and to support a predetermined amount of the coating material. The width of the slot may be dimensioned to support the predetermined amount of the coating material by capillary action, and may narrow from an upstream to a downstream end.

The assembly may include a guide means defining a guide slot located upstream of the container means for aligning the yarn with the slot of the container means. The guide means may have an inclined upstream face. The container means typically defines a plurality of open-ended slots, each dimensioned to receive a section of yarn and to support a predetermined amount of the coating material. The guide means will then typically define a corresponding number of slots.

The assembly may include a storage reservoir having an inlet, and an outlet in liquid communication with the container means. The assembly may also include a pump means for pumping coating material to the storage reservoir, and a pump motor connected to the pump means for driving the pump means.

The assembly may further include a supply controller means for controlling the pump means to replenish the storage reservoir at the same rate as that at which the coating material is removed from the container means by the yarn. The supply controller means may be operable to control the pump motor.

The assembly may also include a main supply reservoir in liquid communication with the inlet of the storage reservoir.

Furthermore, the assembly may include a speed controller means for controlling the rotational speed of the wheel in proportion to the speed at which the length of yarn is moved past the container means by the drive means.

Still further according to the invention there is provided a method of applying a coating material to at least one length of yarn at intermittent locations along the length of yarn, comprising running a length of yarn past a container means for holding a quantity of coating material, and intermittently displacing at least a portion of the length of yarn toward the container means, each displacement bringing a section of the yarn into contact with the coating material to produce intermittently coated sections. The tension of the section of yarn displaced into contact with the coating material may be controlled while said section of yarn is in contact with the coating material.

The speed at which the length of yarn is run past the container means may be determined and the displacement frequency at which the yarn is displaced into contact with the coating material, controlled, the frequency being controlled to change in proportion to the change in speed of the yarn. The coating material in the container means may be replenished at the same rate as that at which it is removed from the container means by the length of yarn.

A coating material in the container means may be replenished in proportion to the speed at which the length of yarn is run past the container means.

A plurality of yarn lengths may be run past the container means simultaneously.

BRIEF DESCRIPTION OF THE DRAWINGS

A more complete appreciation of the invention and many of the attendant advantages thereof will become readily apparent from the following detailed description, particularly considered in conjunction with the drawings in which.

DETAILED DESCRIPTION OF THE INVENTION

For purposes of this invention the term "coating" will be used to refer to a variety of coating substances, e.g. dyes, polymer solutions, scented and unscented waxes and any other coating substance which may be applied to a yarn irrespective of its degree of penetration into the yarn.

For ease of description, however the terms "dye" and "dyeing" will be used to cover all types of coating materials.

Furthermore, the terms "container" and "container means" will be used to refer to any vessel or medium capable of supporting a liquid. This would, for example, also include a pad capable of soaking up and retaining a liquid.

Figure 1:
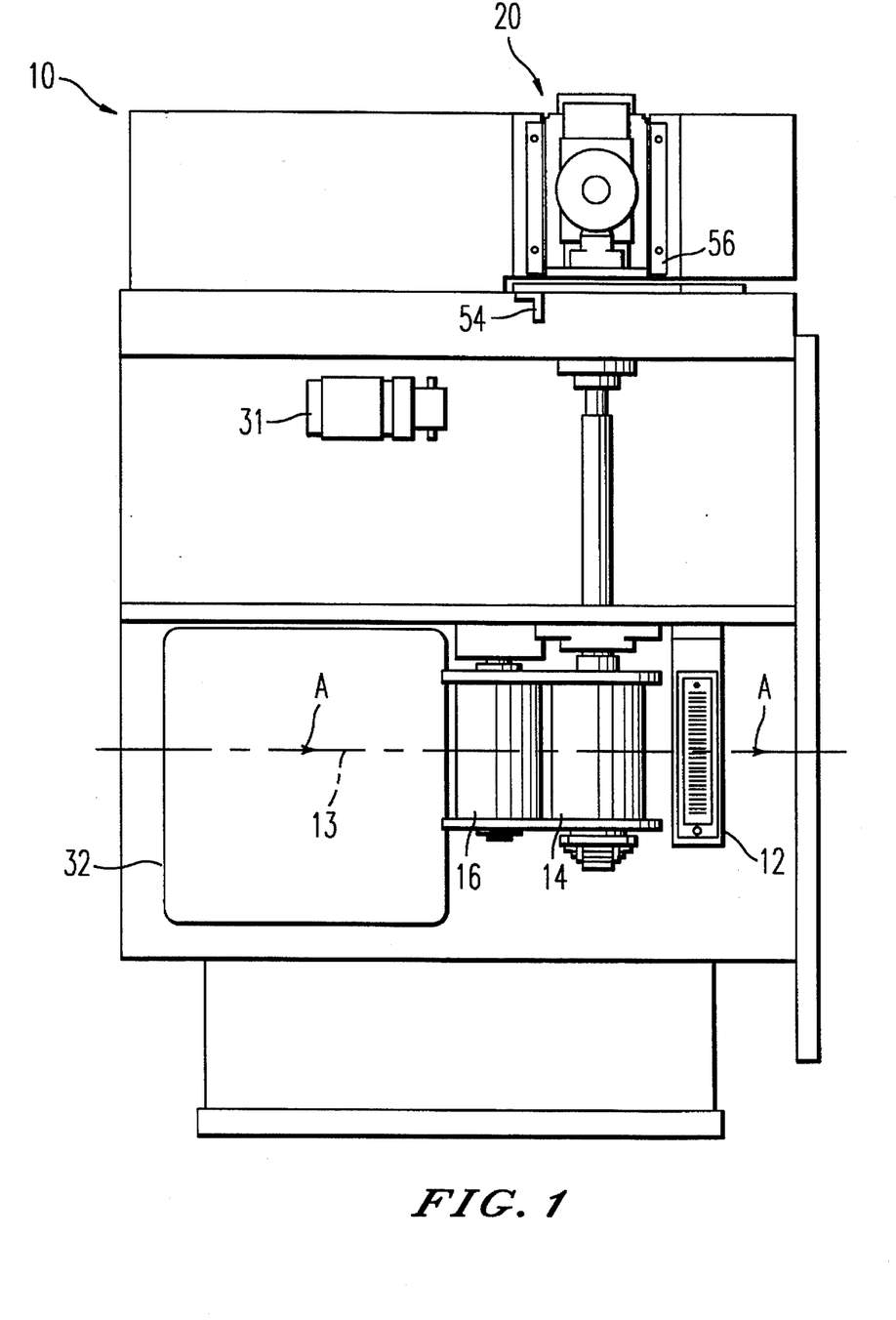
FIG. 1 is a plan view of a yarn coating/dyeing assembly of the present invention.
Figure 2:
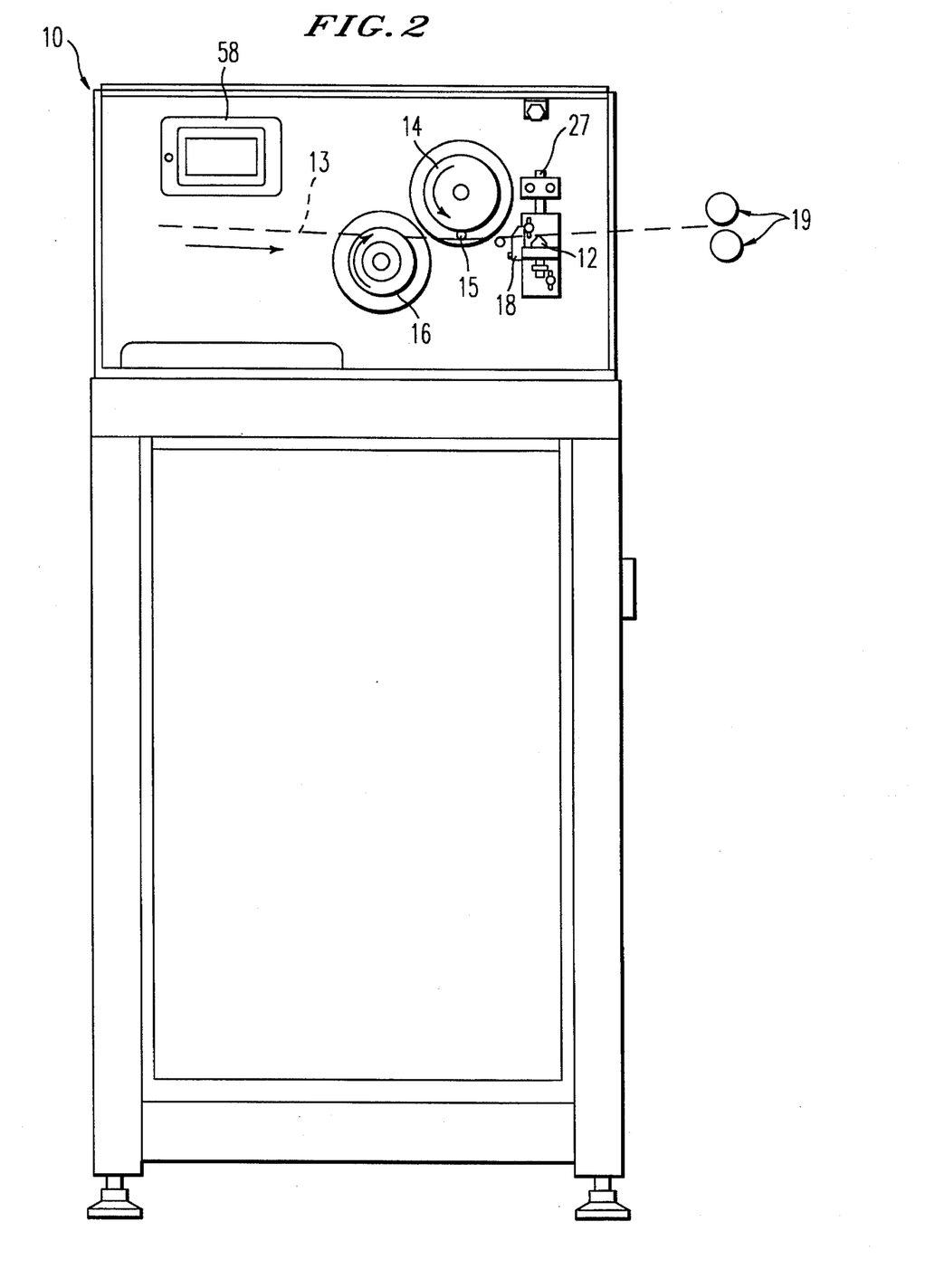
FIG. 2 is a side view of the assembly of FIG. 1.

Referring now to FIGS. 1 and 2, a plan view and side view of the yarn dyeing assembly of the present invention are respectively shown. Thus, for example, in the context of a floss/brush, as discussed above, a coating is applied to maintain the selected portions at a reduced diameter, and also to provide a dyed section to demarcate individual lengths.

As shown in FIG. 1, the yarn dyeing assembly 10 includes a dyeing head or dye applicator 12, which provides dye at intermittent or spaced locations along a continuous length of yarn 13 as the yarn 13 travels in a direction indicated by arrow A. Upstream of the dyeing head 12 is a cam roller 14 which is suitably driven by a drive means indicated generally by reference numeral 20. Further upstream from the cam roller 14, a deflection roller 16 is provided to assist in guiding the yarn 13, and to urge the yarn 13 against the cam roller 14. It is to be understood that the apparatus is preferably utilized for simultaneous dyeing of a plurality of yarns 13, with the plurality of yarns 13 extending in the direction of arrow A, however a single yarn 13 could be dyed if desired.

Referring now to FIG. 2, it will become apparent that the yarns 13 pass over the deflection roller 16, and under the cam roller 14. At least one cam 15 is provided at a peripheral portion of the cam roller 14, such that as the roller 14 rotates, the yarns 13 will be deflected each time the cam 15 passes about the lowermost portion of the path of revolution of the cam 15, with the cam 15 contacting the yarns 13 and deflecting the yarns 13 downwardly. As the yarns 13 are deflected downwardly, they are coated or dyed by the dyeing head 12.

The drive means 20 (FIG. 1) drives the cam roller 14 at a speed dependent upon the yarn travel speed, as well as the desired spacing between dyed portions. This is controlled by means of a magnetic sensor and controller arrangement as is described in greater detail below. The lengths of the dyed portions, in turn, are determined by the configuration of the cam 15. For example, in the floss/brush context, it is desirable to provide selectively dyed portions having a length of approximately 3 inches, with 18 inches of the floss/brush disposed between respective dyed portions. The yarn 13 is driven by feed rollers (schematically indicated on FIG. 2 as 19) which also serve to control the tension of the yarn 13 downstream of the rollers 19. The drive means can include a separate motor, or a shaft extending from a common drive means which operates other components in a floss manufacturing system. For dyeing or coating a floss/brush, the yarn tension during feeding is held at a predetermined level to control absorption of the dye. In the case of an elastic yarn 13, as is envisaged here, the tension typically is such as to maintain the yarn 13 at a reduced diameter. Clearly, however, the tension must be below the tensile strength of the yarn 13 when deflected by the cam roller 14, such that the yarn 13 does not break during the dyeing operation. As is also shown in FIG. 2, a guide means 18 is provided between the cam roller 14 and the dyeing head 12, such that the plurality of yarns 13 are properly positioned with respect to the dyeing head 12 as will become readily apparent hereinafter.

Figure 4:
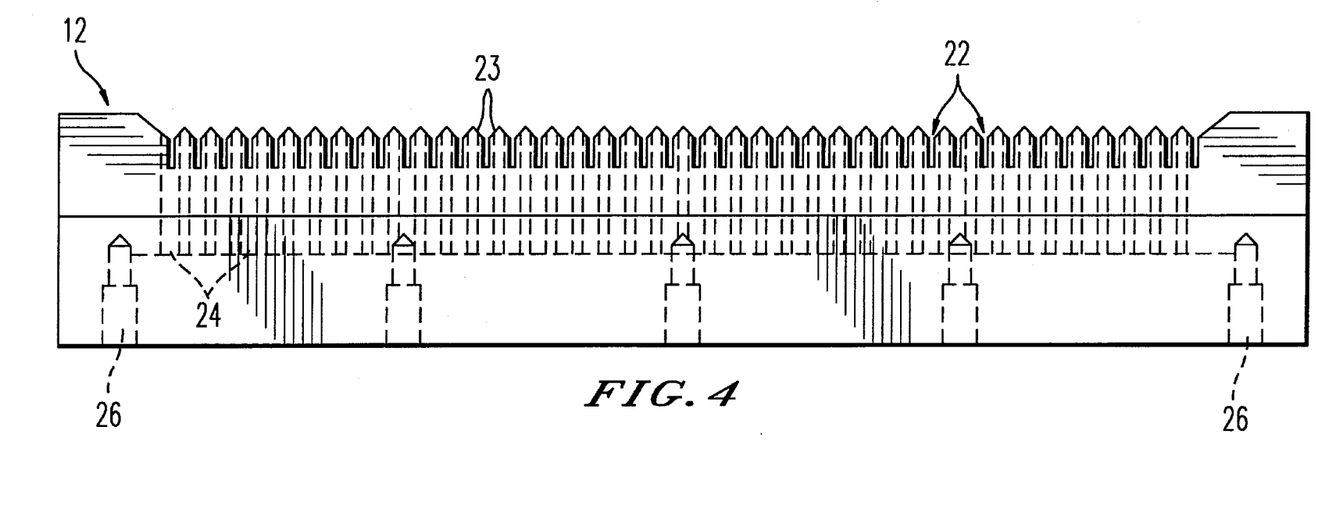
FIG. 4 is a front view of a coating/dye applicator for use in the assembly in accordance with the invention.
Figure 5:
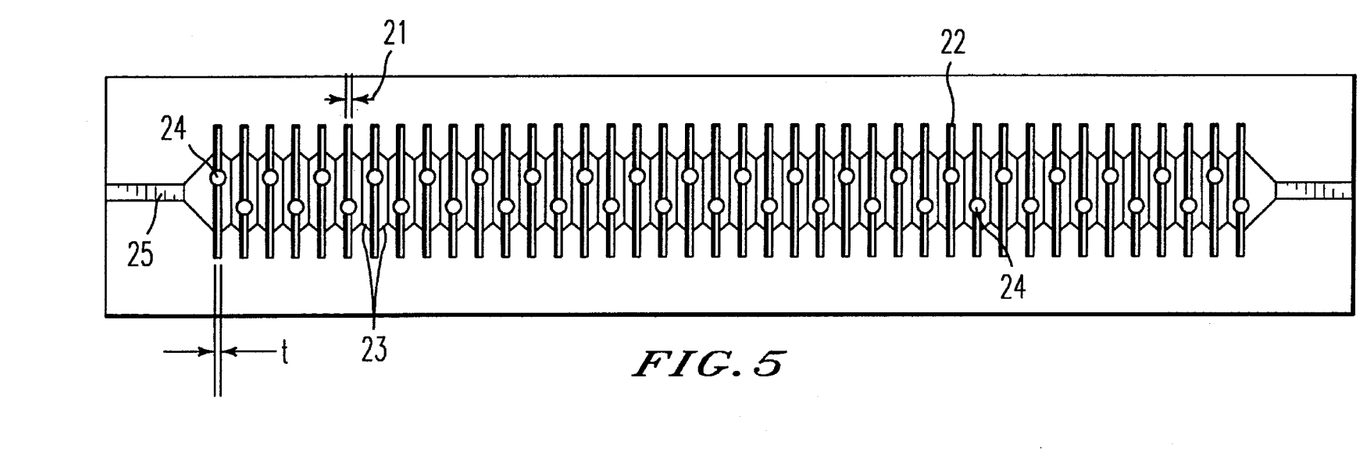
FIG. 5 is a plan view of a coating/dye applicator for use in the assembly in accordance with the invention.
Figure 6:
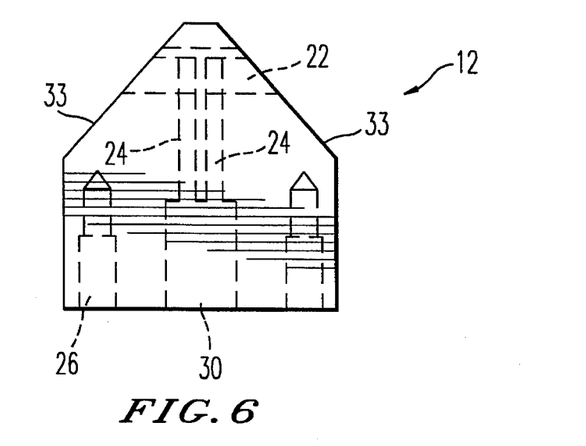
FIG. 6 is a side view of a coating/dye applicator for use in the assembly in accordance with the invention.

Referring to FIGS. 4, 5 and 6, details of the dyeing head 12 will now be described. FIG. 4 shows a front view of the dyeing head 12, in which a plurality of slots or grooves 22 are provided for a corresponding number of yarns 13 which are to be dyed simultaneously. In the embodiment of FIG. 4, 40 slots are provided, thereby allowing for the simultaneous selective dyeing of 40 yarns. The upper open ends of the slots or grooves 22 are defined by inclined surfaces 23 which support the yarns. The lower closed ends of the slots 22 are defined by a pair of spaced apart, substantially parallel sides, extending from a base. The inclined surfaces 23 insure that any splices or other irregularities in the yarns 13 do not interrupt the process, e.g. by catching in the slots 22 and thereby breaking the yarn 13. In the event of an irregularity the inclined surfaces 23 will urge the yarn 13 upwardly to accommodate the irregularity. A plurality of bolt holes 26 are provided for mounting the dyeing head 12 by means of mounting bolts (not shown). By loosening the mounting bolts, and manipulating an adjustment screw 27 (FIG. 2) the height of the head 12 may be adjusted to increase or decrease the height of the head 12 relative to the yarn 13.

Each slot 22 includes a liquid supply conduit 24 which supplies the dye upwardly into the slots 22, such that the slots 22 are constantly supplied with the dye. In the embodiment shown in FIGS. 4 to 6, the supply conduits 24 are alternatingly staggered, thereby allowing the supply conduits 24 to be formed of a sufficient size constantly to flood the slots 22, while increasing the structural integrity of the dyeing head 12. In this embodiment the supply conduits 24 are formed with a diameter of 0.05 to 0.12 inches, preferably 0.07 to 0.09 inches, depending on the viscosity of the dye or coating material. The slots 22 may be formed of a sufficiently small width 21 (e.g. 0.015 inches), such that the dye is constantly maintained within the entire length of the slots 22 by capillary action. Instead, as in this embodiment, a pump may be controlled to supply the appropriate amount of dye to replenish the slots 22 at the same rate as that at which the dye is removed from the slots 22 by the yarns 13.

As regards the capillary action embodiment, it has been recognized that a dye/coating can be provided for selected portions of yarns by utilizing grooves which maintain the dye by capillary action. Capillary action depends upon two factors including: (1) the cohesion of the liquid molecules; and (2) the adhesion of the molecules to the surface of a solid, in this case the material of the dyeing head.

Thus, the actual width of the grooves can vary as coatings or liquids to be applied to the yarn 13 vary, or if different materials for forming the dyeing head 12 are selected. Brass and stainless steel have, for instance, been found to work well as materials for the head 12. It will be appreciated that the positioning of the conduits 28 may take a variety of configurations. In one embodiment, illustrated in FIGS. 7 to 9, found to work particularly well, the conduits 28 are spaced along a common straight line running slightly to one side of the longitudinal axis of the head 12, closer to its upstream end. This provides for a very uniform coating for all the yarns.

Figure 7:
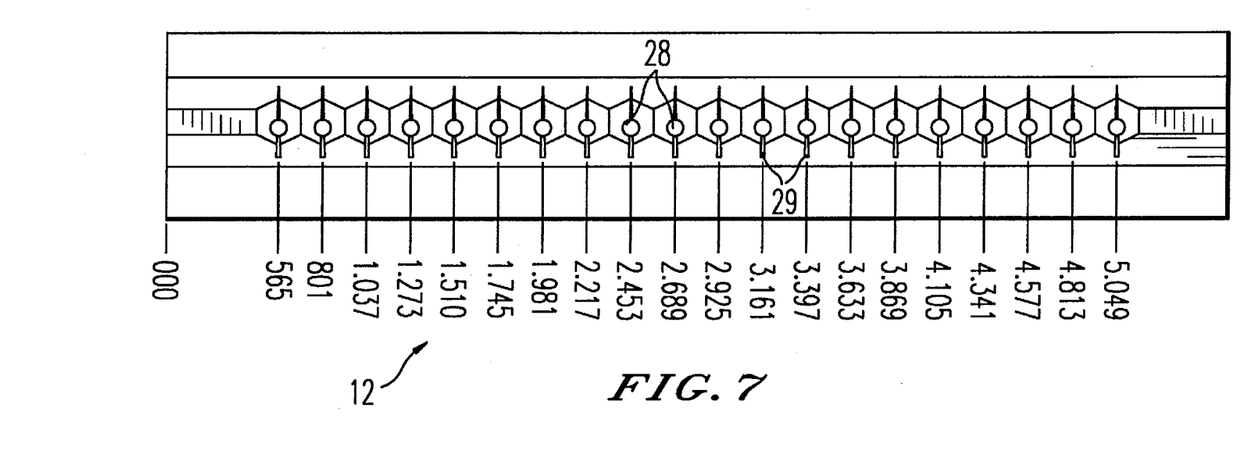
FIG. 7 is a plan view of another embodiment of a coating/dye applicator in accordance with the invention.
Figure 8:
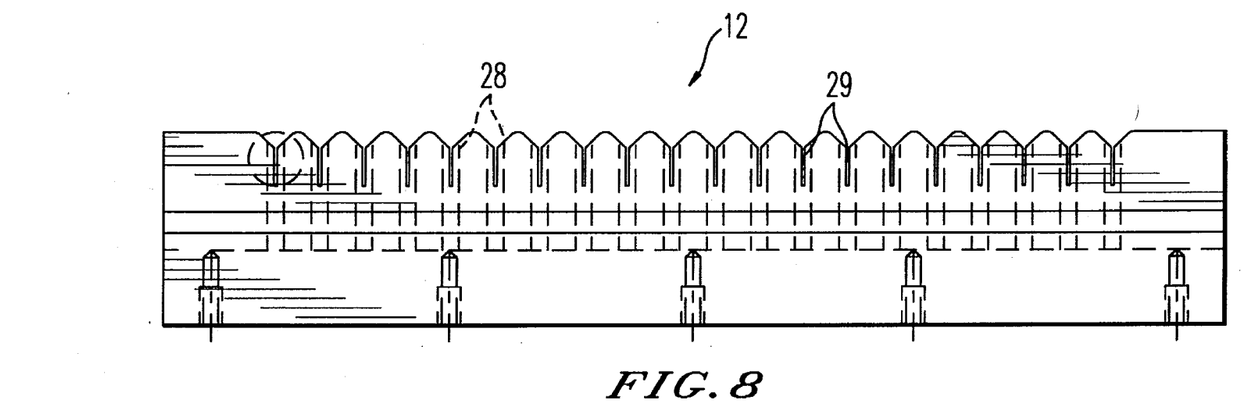
FIG. 8 is a front view of the coating/dye applicator of FIG. 7.
Figure 9:
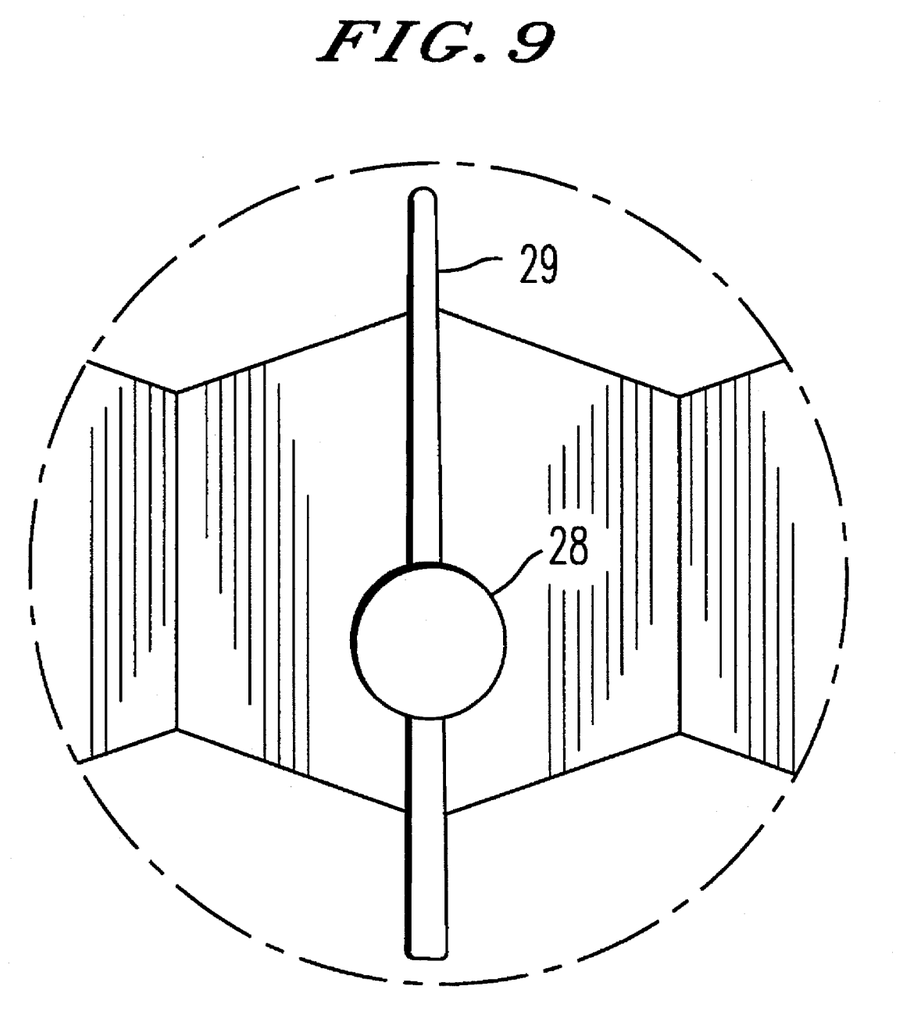
FIG. 9 is a detailed plan view of part of the coating/dye applicator of FIG. 7.

In this embodiment the conduits 28 have a diameter of 0.07 inches and the grooves 29 tapered from 0.018 inches at their upstream ends to 0.011–0.012 inches at their downstream ends. This tapered shape provides for better retention of the coating material.

Referring again to FIG. 6, the supply conduits 24 are in flow communication with a dye storage reservoir 30, such that the supply conduits 24 supply the dye upwardly from the storage reservoir 30 to the slots 22. A ceramic piston pump 31 (FIG. 1) replenishes the reservoir 30 by continuously supplying dye from a main supply reservoir 32 to the reservoir 30 via a primary supply conduit (not shown). The primary supply conduit feeds the dye into the reservoir 30 by means of an inlet (not shown) provided in a lower wall of the reservoir 30. The conduits 24 are thus constantly supplied with dye and act as temporary storage reservoirs for supplying dye to the slots 22. The dye level in the conduits accordingly fluctuates as dye is continuously supplied from the reservoir 30 and is intermittently removed by the yarn 13. As is also shown in the side view of FIG. 6, the upstream and downstream faces 33 of the dyeing head 12 are inclined, resulting in the hexagonal appearance of the open ends of the slots 22 when seen in plan view (FIG. 5). The inclined configuration serves to urge the yarn 13 upwardly in the event of an irregularity in the yarn 13, thus causing the yarn 13 to ride higher on the inclined surfaces 23 as was described above.

Figure 10:
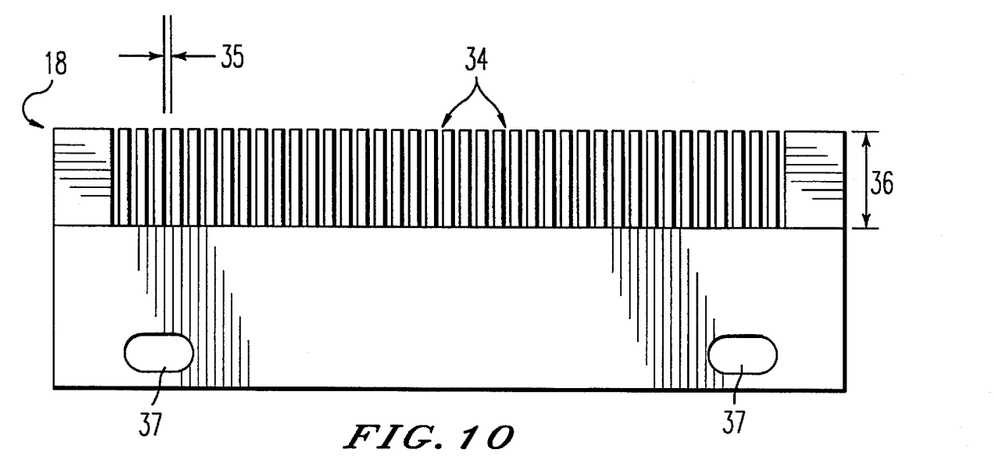
FIG. 10 is a front view of a comb-like guide means for guiding a plurality of yarns into the coating/dye applicator.
Figure 11:
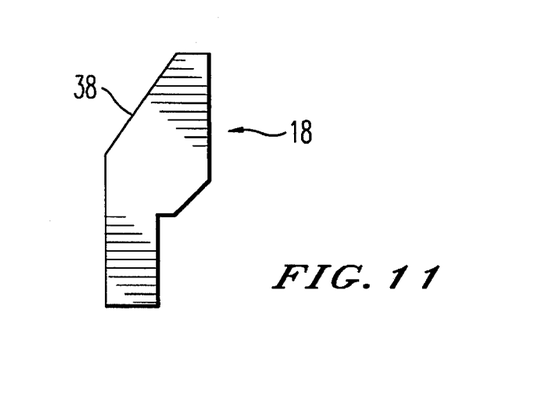
FIG. 11 is a side view of the guide means of FIG. 10.

Referring to FIGS. 10 and 11, the guide means 18 (disposed adjacent the dyeing head 12 as shown in FIG. 2) includes a comb-like structure, with a plurality of guide slots 34 corresponding to the number of slots provided in the dyeing head 12. The guide slots 34 have a width 35 which typically is larger than the width 21 of the slots 22 or the maximum width of the slots 29, such that the yarns can be guided by the guide slots 34, without rubbing excessively against the guide slots 34, and to accommodate small irregularities in the yarn. The yarns are thus suitably positioned with respect to the slots 22, 29 by the guide slots 34 of the comb-like structure, and by the inclined surfaces 23 of the dyeing head 12. A suitable width 35 of the guide slots 34 is for example 0.03 inches. The height 36 of the guide slots 34 is sufficient such that the yarns 13 are retained in the guide slots 34 irrespective of whether or not they are deflected by the cam 15. Mounting apertures 37 are provided such that the guide means 18 can be mounted directly on the dyeing head 12. As shown in the side view of the guide means 18 (FIG. 11), the guide means 18 is shaped to be mounted closely adjacent to the dyeing head 12. As with the head 12, the guide means 18 has an inclined upstream face 38 to allow the yarn to ride up on the guide means 18 in the event of an oversized irregularity in the yarn 13 being encountered.

Figure 12:
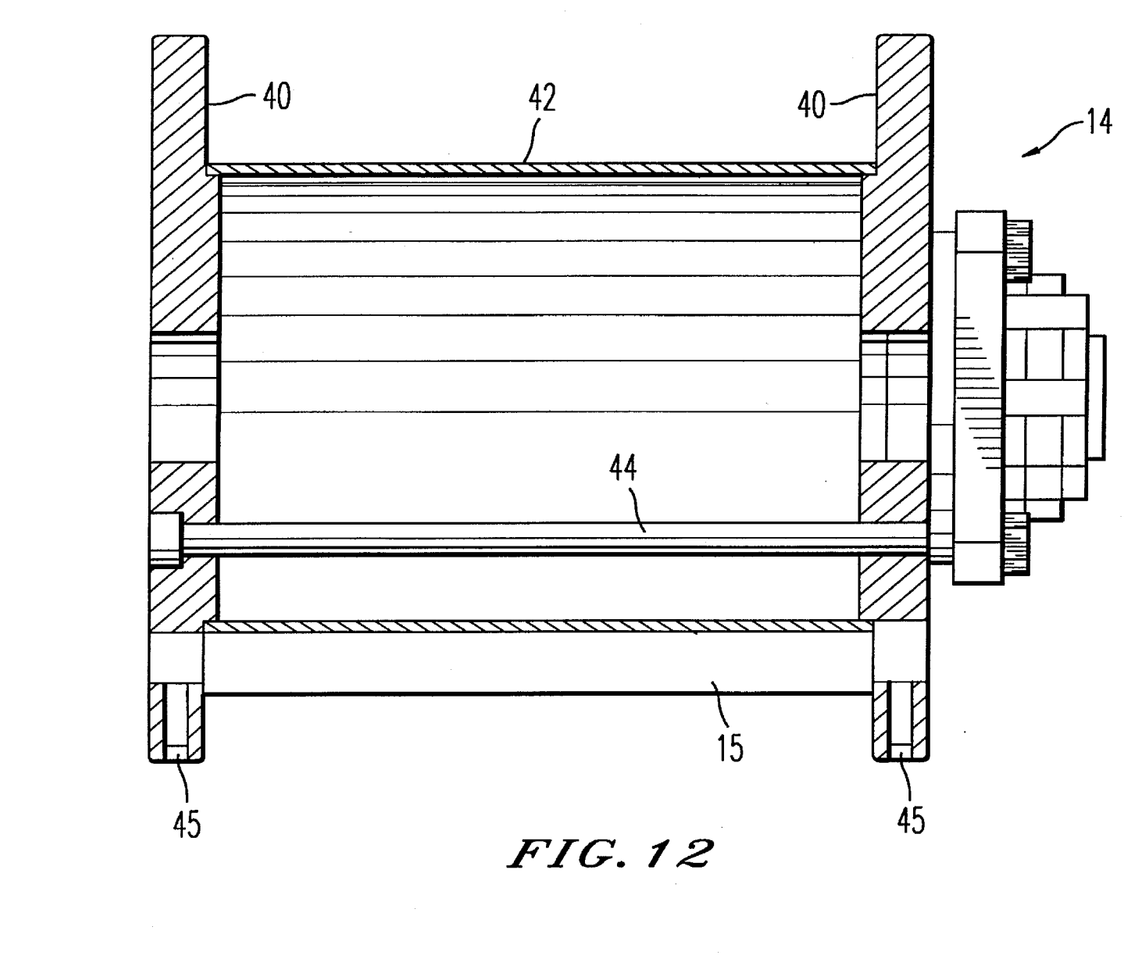
FIG. 12 is a side view of a deflection roller in partial cross-section.

Referring now to FIG. 12, a front view of the cam roller 14 is shown in partial cross-section. The roller 14 includes a pair of end plates 40 secured to opposite ends of a roller cylinder having a surface 42. The roller 14 is maintained by a plurality of bolts 44. Three bolts 44 were found to be adequate in practice. The cam 15 in the form of a rod, is secured to the end plates 40, by means of suitable fasteners. In the embodiment illustrated, spigot-like ends of the cam 15 are received in apertures in the plates 40 and retained by means of retention clips 45.

Figure 3:
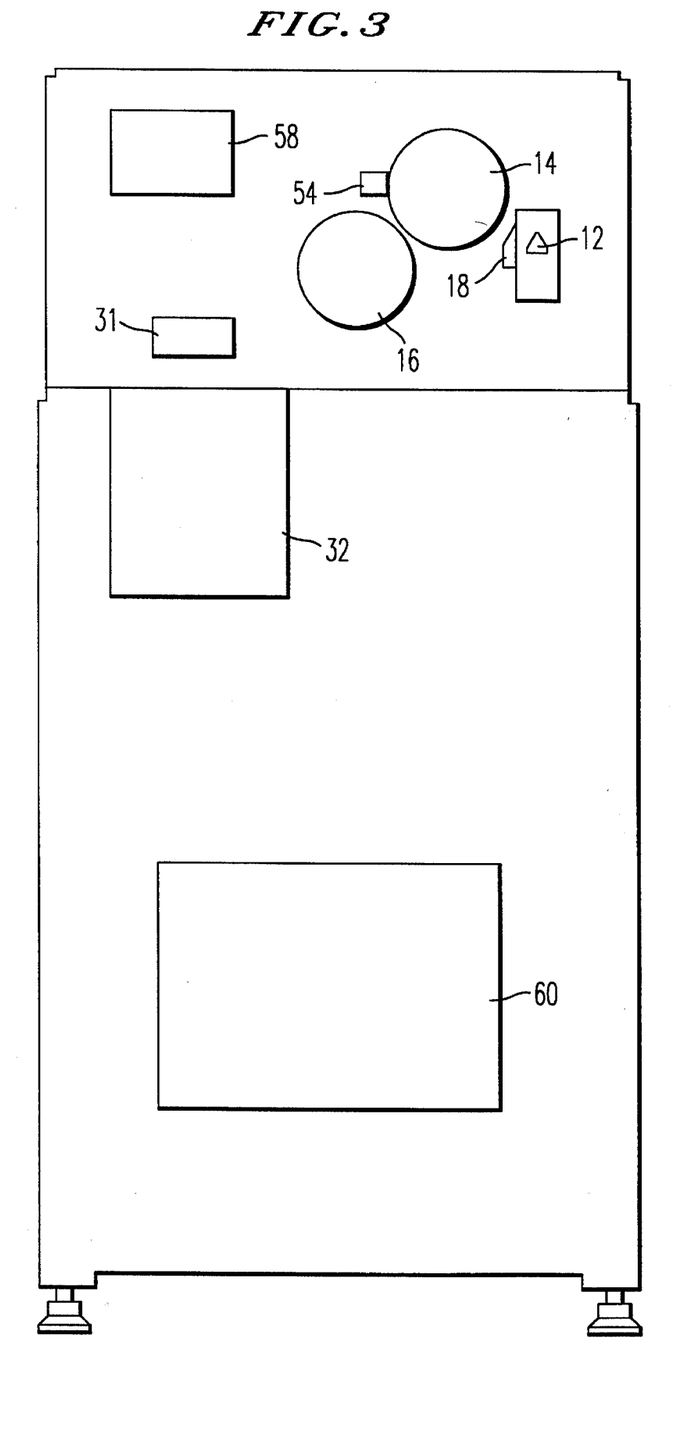
FIG. 3 is a schematic side view of the assembly of FIG. 2 showing the location of some of the components of the assembly.

As mentioned above, and referring again to FIGS. 1–3, the drive means 20 is controlled by a magnetic sensor and controller arrangement. Referring to FIG. 1, a sensor (not shown) detects the yarn speed. A second magnetic sensor 54 monitors the rotational speed of the cam drive gear 56. The magnetic signal from the sensor 54 is converted into a 4–20 mA output signal which is, in turn, shaped by a programmable controller 58 (FIGS. 2 and 3) and used to control the rotational speed of the cam roller 14. In addition, the pump 31 is controlled in a manner described below. The 4–20 mA output signal is sent to a stepper motor controller 60 (FIG. 3). This controls the speed of a stepper motor (not shown) which drives the pump 31. A digitally adjustable slope multiplier, adjustable to 0.1% of full scale, allows adjustment of the stepper motor speed.

Furthermore, by adjusting the angle between the stepper motor and the pump 31, the piston stroke and consequently the displacement of the piston may be adjusted. Thus the amount of dye supplied by the pump 31 and the spacing between dyed portions can be controlled in sympathy with and as a function of the yarn speed.

The replenishment of the dye in the slots can instead be related to the depletion of the dye from the slots by the yarns 13 by monitoring the level of the dye in the slots, for example by using an optical sensor. The signals from the sensor are then fed to a microprocessor to control the stepper motor speed.

In order to adjust the length of the dyed portions, the cam 15 may be replaced with a suitably shaped cam. The length of application is fine-tuned by adjusting the height of the head 12 by loosening the mounting bolts and manipulating the adjustment screw 27 (FIG. 2). Clearly, numerous modifications and variations of the present invention are possible in the light of the above teachings. It is therefore to be understood that within the scope of the appended claims, the invention may be practiced otherwise than as specifically described herein.

The invention claimed is:

1. A coating applicator for applying a coating material to yarn comprising a container wherein the container has at least one open-ended slot, said at least one slot having a base and an open end for receiving a section of yarn, and said at least one slot being defined by a pair of spaced apart, substantially parallel sides, extending from the base and spaced sufficiently closely to each other to support a predetermined amount of a coating material by capillary action, wherein the container has an upstream and a downstream face, at least the upstream face of the container being inclined inwardly towards the open end.

2. A yarn coating applicator of claim 1, wherein said at least one slot includes an upper portion at the open end, defined by a pair of inclined outwardly extending surfaces.

3. A yarn coating assembly of claim 1, wherein the at least one slot narrows from the upstream face to the downstream face.

4. A yarn coating assembly for applying a coating material to a length of yarn comprising a container means for holding a quantity of the coating material, said container means defining an open ended slot having a width sufficient to accommodate the thickness of the yarn and said slot being dimensioned to support the predetermined amount of coating material by capillary action, a drive means for moving the length of yarn past the container means, and displacement means for intermittently displacing at least a portion of the yarn toward the container means to intermittently bring a section of the yarn into contact with the coating material.

5. An assembly of claim 4, wherein the displacement means comprises a cam on a rotatable wheel, the cam having a cam surface positioned relative to the yarn such that, upon rotation of the wheel, the yarn is urged into contact with the coating material by the cam surface engaging the yarn, and when the cam surface is not in contact with the yarn, the yarn is not in contact with the coating material.

6. An assembly of claim 5, wherein the cam is removably mounted on the wheel.

7. An assembly of claim 5, wherein the assembly includes a speed controller means for controlling the rotational speed of the wheel in proportion to the speed at which the length of yarn is moved past the container means by the drive means.

8. An assembly of claim 4, wherein the slot narrows from an upstream to a downstream end.

9. An assembly of claim 4, wherein the assembly includes a guide means defining a guide slot located upstream of the container means for aligning the yarn with the slot of the container means.

10. An assembly of claim 9, wherein the guide means has an inclined upstream face.

11. An assembly of claim 4, wherein the container means defines a plurality of open-ended slots, each dimensioned to receive a section of yarn and to support a predetermined amount of the coating material.

12. An assembly of claim 11, wherein the assembly includes a storage reservoir having an inlet, and an outlet in liquid communication with the container means.

13. An assembly of claim 12, wherein the assembly includes a pump means connected to the storage reservoir for supplying coating material to the storage reservoir and a pump motor connected to the pump means for driving the pump means.

14. An assembly of claim 13, wherein the assembly includes a supply controller means for controlling the pump means to replenish the storage reservoir at the same rate as that at which the coating material is removed from the container means by the yarn.

15. An assembly of claim 14, wherein the assembly includes a main supply reservoir in liquid communication with the inlet of the storage reservoir.

* * * * *